United States Patent [19]

Tano et al.

[11] Patent Number: 4,822,359
[45] Date of Patent: Apr. 18, 1989

[54] INTRAOCULAR LENS WITH COATED DIAMOND-LIKE CARBON FILM

[75] Inventors: Yasuo Tano; Hisashi Hosotani; Naoji Fujimori; Keizo Harada, all of Hyogo, Japan

[73] Assignee: Sumitomo Electric Industries, Ltd., Osaka, Japan

[21] Appl. No.: 156,752

[22] Filed: Feb. 18, 1988

[30] Foreign Application Priority Data

Feb. 19, 1987 [JP] Japan ................................ 62-36681

[51] Int. Cl.⁴ ............................ A61F 2/16; A01N 1/02
[52] U.S. Cl. ............................................ 623/6; 427/2
[58] Field of Search ........................................ 623/4–6; 427/2

[56] References Cited

U.S. PATENT DOCUMENTS

| 4,045,125 | 8/1977 | Farges. | |
|---|---|---|---|
| 4,240,163 | 12/1980 | Galin | 623/6 |

FOREIGN PATENT DOCUMENTS

| 0030792 | 6/1981 | European Pat. Off. . | |
|---|---|---|---|
| 0161765 | 11/1985 | European Pat. Off. . | |
| 2705234 | 8/1978 | Fed. Rep. of Germany | 623/5 |
| 3428895 | 2/1986 | Fed. Rep. of Germany | 623/6 |
| 2271589 | 12/1975 | France . | |

Primary Examiner—Ronald L. Frinks
Attorney, Agent, or Firm—Cushman, Darby & Cushman

[57] ABSTRACT

An intraocular lens comprises an artificial crystalline lens and a diamond-like carbon film coated on the surface of the artificial crystalline lens.

2 Claims, 1 Drawing Sheet

INTRAOCULAR LENS WITH COATED DIAMOND-LIKE CARBON FILM

BACKGROUND OF THE INVENTION

The present invention relates to an intraocular lens which is to be implanted in place of the natural eye's crystalline lens that has been removed in surgical operations on cataract and so on.

In surgical operations on cataracts, the crystalline lens is removed from the natural eye and replaced by an artifical crystalline lens. Conventionally, intraocular lenses made of polymethyl methacrylate resins (hereinafter referred to as PMMA resins), which are used for the surgical operations, are widespread in the U.S. and many other countries in the world.

Such an intraocular lens is implanted in a location that is close to the place where the natural eye's crystalline lens was positioned so that the state of an image focused on the retina is very close to that attained by the normal eye. Accordingly, the intraocular lens is particularly suitable for use as artificial crystalline lenses from the viewpoint of the restoration of the patient's vision after operation. Also, the intraocular lenses require no daily care and are preferred for aged people who are frequent victims of cataract.

The application of intraocular lenses made of PMMA resins is increasing today and further improvements in their properties such as biocompatibility and transparency are needed.

Conventional intraocular lenses made of PMMA resins have very high degrees of light transmission in the visible range and biocompatibility and have been used in clinical applications. However, they suffer from the disadvantage that they are transparent not only to visible light but also to light in the ultraviolet and near ultraviolet (260–350 nm) regions.

FIG. 3 shows the transmittance characteristics of a prior art intraocular lens made of PMMA resin. As shown in FIG. 3, the conventional intraocular lens transmits ultraviolet rays at wavelengths below 250 nm and its transmittance of light in the near ultraviolet range longer than 250 nm is sharply increased to at least 90%. If such as intraocular lens is implanted in a patient's eye, his eyeball, in particular, the optic nerve may be damaged by ultraviolet radiation. There also is a problem in association with visual sensation; that is, the eye fitted with this lens which transmits light in the ultraviolet and near ultraviolet regions produces a more bluish sensation than the normal eyeball.

In order to solve these problems, the incorporation of uv absorbers and/or pigments in PMMA resins has been attempted but it has turned out that these additives change or reduce the biocompatibility of the intraocular lens, with some of them being particularly undesirable since they are potentially carcinogenic.

SUMMARY OF THE INVENTION

An object, therefore, of the present invention is to provide a highly biocompatible intraocular lens that does not transmit any of the rays in the ultraviolet and near ultraviolet regions and which yet retains high transmittance of visible rays of light.

The present inventors conducted intensive studies in order to develop an intraocular lens that is free from the aforementioned problems with the prior art products and which is most close to the normal eye's crystalline lens. The present invention has been accomplished as a result of these efforts and solves the problems by coating a diamond-like carbon film on the surface of an artificial crystalline lens made of such a material as a PMMA resin.

According to the present invention, there is provided an intraocular lens having the surface of an artificial crystalline lens coated with a diamond-like carbon film. The artificial crystalline lens is preferably made of a polymethyl methacrylate. The diamond-like carbon film coated on the surface of the artificial crystalline lens preferably has a thickness in the range of 10–100 nm.

In order to deposit diamond-like carbon on a PMMA resin, the diamond-like carbon film according to the present invention is preferably formed by some suitable method such as ion beam deposition, sputtering or RF decomposition that are capable of forming a diamond-like carbon film at low temperatures.

An artificial crystalline lens made of such a material as PMMA resin which is coated with a diamond-like carbon film on its surface in accordance with the present invention has the ability to block the transmission of light in the ultraviolet and near ultraviolet regions, while permitting light in the visible range to be transmitted. Further, the surface coating which is made of a carbon material has only a small irritating effect on living tissues and good biocompatibility to the tissues so that the intraocular lens of the present invention is highly advantageous as a biomaterial.

DETAILED DESCRIPTION OF THE PREFERRED EMBODIMENTS

Figure 1:
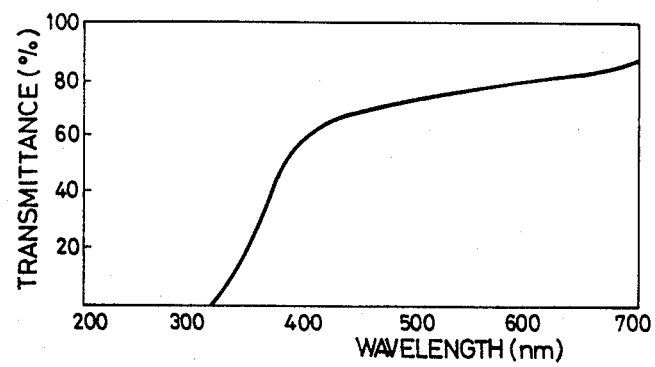
FIG. 1 is a graph showing the light transmission characteristics of an intraocular lens according to one embodiment of the present invention.

FIG. 1 is a graph showing the light transmittance of an intraocular lens having a diamond-like carbon film coated in a thickness of 20 nm on the surface of an artificial crystalline lens made of a PMMA resin. As shown in FIG. 1, the intraocular lens furnished with the diamond-like carbon film is transparent only to the light in the visible and infrared regions.

The quantity of light in the shorter wavelength range that is transmitted through the intraocular lens of the present invention can be adjusted by controlling the thickness of the diamond-like carbon film. If the thickness of the film is less than 10 nm, light transmission is increased on the shorter wavelength side. Furthermore, pinholes in the thin film will permit some transmission of near ultraviolet light. Accordingly, the diamond-like carbon film is unable to exhibit its intended effect, i.e., blocking the light in the ultraviolet and near ultraviolet regions. If, on the other hand, the film thickness exceeds 100 nm, the intraocular lens will absorb not only undesired light but also the visible light which should be transmitted. In addition, the cost of forming the diamond-like carbon film is increased. Therefore, according to the present invention, a film thickness that is effective for the purpose of admitting desired visible light while blocking undesired light in the near ultraviolet region may be determined within the range of 10–100 nm.

Cataracts develop mostly in the eyes of aged people and the ability of the crystalline lens to admit transmission of light in the short wavelength range decreases with age. When an intraocular lens that is capable of transmitting a large quantity of rays at wavelengths shorter than 500 nm is implanted in the eyes of aged patients who have received a surgical operation to remove cataracts, most of the patients comment that they "see everything bluish". In consideration of this fact together with the elements discussed in the foregoing paragraph, the thickness of the diamond-like carbon film formed on the intraocular lens of the present invention is to be determined within the range of 10–100 nm.

In the present invention, the diamond like carbon film is preferably formed by a low-temperature processes such as ion beam deposition, sputtering and RF decomposition. In the ion beam deposition method, carbon ions produced by sputtering a carbon electrode is accelerated by such a mechanism as the difference in pressure or magnetic field and driven toward the surface of a PMMA resin so as to deposit diamond-like carbon on the resin surface. In the RF decomposition method, a plasma is produced by applying an electric field oscillating at high frequency between electrodes and a negative voltage is superposed on the deposition side, that is, on the electrode where the artificial crystalline lens is disposed. As a mixture of hydrogen gas and a hydrocarbon gas is supplied between the electrodes, the hydrocarbon gas is ionized by the plasma and the resulting ion is accelerated toward the negative electrode to deposit diamond-like carbon on the artificial crystalline lens.

The carbon film thus formed is essentially in the form of a amorphous matrix in which diamond-like crystals are dispersed. This diamond-like carbon film has a high degree of biocompatibility and presents no problem of carcinogenicity. Furthermore, this diamond-like carbon film has a high degree of hardness and displays high transmittance of light in both visible and infrared regions.

The artificial crystalline lens of the intraocular lens of the present invention is preferably made of a PMMA resin. It should, however, be noted that the material of the artificial crystalline lens is in no way limited to PMMA resins and that the present invention also includes within its scope those intraocular lenses having a diamond-like carbon film formed on the surface of artificial crystalline lenses made of other suitable materials.

The following example is provided for the purpose of further illustrating the present invention but is in no way to be taken as limiting.

EXAMPLE

Intraocular lens samples were fabricated by forming diamond-like carbon films in varying thicknesses (5 nm, 10 nm, 40 nm, 100 nm and 750 nm) on artificial crystalline lenses of PMMA resin by a RF decomposition technique that was performed under the conditions shown in Table 1.

TABLE 1

| | |
|---|---|
| $CH_4$ gas pressure | $1 \times 10^{-3}$ Torr |
| RF output | 200 W |
| Substrate temperature | 100° C. |

Figure 2:
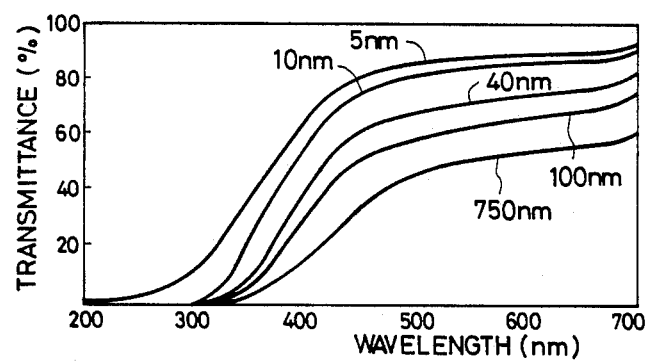
FIG. 2 is a graph showing the light transmission characteristics of the intraocular lens of the present invention as a function of the thickness of a diamond-like carbon film.
Figure 3:
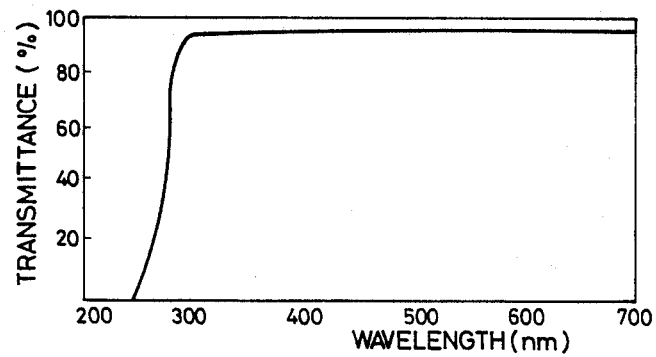
FIG. 3 is a graph showing the light transmission characteristics of a conventional intraocular lens made of a PMMA resin.

The light transmittance characteristics of the individual samples were investigated and the results are shown graphically in FIG. 2.

As is clear from FIG. 2, the artificial crystalline lens coated with a diamond-like carbon film in a thickness of 5 nm is not satisfactory as an intraocular lens since it admits some transmission of ultraviolet light harmful to the optic nerve and retina. With a diamond-like carbon film of 10 nm thick, the absorption edge exceeds 300 nm and the artificial crystalline lens substantially blocks the light in the near ultraviolet region while admitting high transmission of visible light. If the carbon film thickness is 100 nm, the lens completely blocks the light in the near ultraviolet region and yet retains the high transmission of visible light. As the film thickness exceeds 100 nm, transparency to visible light is gradually decreased and the intraocular lens will lose its function as an artificial crystalline lens.

It was therefore established from the experimental results shown in FIG. 2 that the appropriate thickness of the diamond-like carbon film to be deposited on the artificial crystalline film made of a PMMA resin is within the range of 10–100 nm.

As described above, an artificial crystalline lens made of a PMMA resin or some other suitable material that is coated with a diamond-like carbon film according to the present invention provides an intraocular lens that effectively blocks rays of light in the ultraviolet and near ultraviolet regions to produce visual sensation of color that is close to what is attainable by the natural eye's crystalline lens. Therefore, the intraocular lens of the present invention can be used without any potential damage to the retina by ultraviolet radiation. The diamond-like carbon film is hard and resistant to scratching that may occur during handling of the lens. The intraocular lens of the present invention has the additional advantage of affording high biocompatibility without causing an problem such as carcinogenicity.

What is claimed is:

1. An intraocular lens comprising an artificial crystalline lens, and a diamond-like carbon film coated on the surface of said artificial crystalline lens said film having a thickness in the range of approximately 10–100 nm.

2. An intraocular lens according to claim 1 wherein said artificial crystalline lens is made of a polymethyl methacrylate resin.

* * * * *